United States Patent [19]

Sullivan

[11] 4,317,833
[45] Mar. 2, 1982

[54] METHOD FOR THE REDUCTION OF EXCESS GASTRIC ACID SECRETION

[75] Inventor: Thomas J. Sullivan, Thrussington, England

[73] Assignee: Fisons Limited, London, England

[21] Appl. No.: 101,464

[22] Filed: Dec. 10, 1979

[30] Foreign Application Priority Data

Dec. 27, 1978 [GB] United Kingdom ............... 49995/78

[51] Int. Cl.³ .................... A61K 33/08; A61K 31/46; A61K 31/35
[52] U.S. Cl. .................................. 424/283; 424/157; 424/265
[58] Field of Search ........................ 424/283, 157, 265

[56] References Cited

U.S. PATENT DOCUMENTS 4,152,448 5/1979 Wardell .............................. 424/283
4,159,273 6/1979 Brown ................................ 424/283

FOREIGN PATENT DOCUMENTS 7508162 1/1976 Netherlands ........................ 424/283

Primary Examiner—Frederick E. Waddell
Attorney, Agent, or Firm—Merriam, Marshall & Bicknell

[57] ABSTRACT

There is described a method for the prevention or inhibition of gastric acid secretion, and/or the treatment of conditions involving excess gastric acid secretion, which method comprises administration of a compound of the formula I,

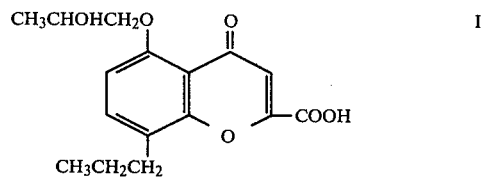

or a pharmaceutically acceptable derivative thereof (as active ingredient), to a patient having, or liable to have, excess gastric acid secretion and/or a condition involving excess gastric acid secretion, or in whom a reduction in gastric acid secretion is desired.

8 Claims, No Drawings

METHOD FOR THE REDUCTION OF EXCESS GASTRIC ACID SECRETION

This invention relates to a new therapeutic method.

According to the invention there is provided a method for the prevention or inhibition of gastric acid secretion, and/or the treatment of conditions normally involving excess gastric acid secretion, which method comprises administration of a compound of the formula I,

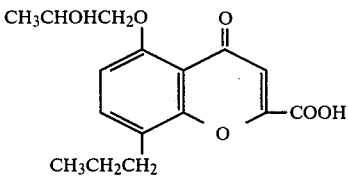

or a pharmaceutically acceptable derivative thereof (as active ingredient), to a patient having, or liable to have, excess gastric acid secretion and/or a condition normally involving excess gastric acid secretion, or in whom a reduction in gastric acid secretion is desired.

Pharmaceutically acceptable derivatives of the compound of formula I include pharmaceutically acceptable salts, esters and amides of the 2-carboxylic acid group. Suitable salts include ammonium, alkali metal (e.g. sodium, potassium and lithium) and alkaline earth metal salts (e.g. calcium or magnesium), and salts with suitable organic bases, e.g. salts with lower alkylamines such as methylamine or ethylamine, with substituted lower alkylamines, e.g. hydroxy substituted alkylamines or with simple monocyclic nitrogen heterocyclic compounds, e.g. piperidine or morpholine. Suitable esters include simple lower alkyl (e.g. C 1 to 10) esters, esters derived from alcohols containing basic groups, e.g. di-lower alkyl (e.g. C 1 to 10) amino substituted alkanols, and acyloxy alkyl esters, e.g. a lower acyl-lower alkyl ester, or a bis-ester derived from a di-hydroxy compound, e.g. a di(hydroxy-lower alkyl)ether. The pharmaceutically acceptable salts of the basic esters, e.g. the hydrochloride, may also be used. The esters may be made by conventional techniques, e.g. esterification or transesterification. We prefer to use the free acid of formula I, or a salt, e.g. the sodium salt, thereof.

The drug (i.e. the compound of formula I or the pharmaceutically acceptable derivative thereof) may be administered to mammals, particularly humans, by conventional means, e.g. rectally or orally.

The drug may also be administered intravenously, but only at dosages of up to 500 mg.

In order to produce suitable compositions the drug is worked up with inorganic or organic pharmaceutically acceptable adjuvants or excipients. Examples of such adjuvants are:

For tablets capsules and dragées; microcrystalline cellulose, calcium phosphate, diatomaceous earth, a sugar such as lactose, dextrose or mannitol, talc, stearic acid, starch, sodium bicarbonate and/or gelatin; for suppositories, natural or hardened oils or waxes; and for inhalation compositions, coarse lactose and/or propellent gasses. The compound of formula I, or the pharmaceutically acceptable derivative thereof, preferably is in a form having a mass median diameter of from 0.01 to 10 microns. The compositions may also contain suitable preserving, stabilising and wetting agents, solubilizers, sweetening and colouring agents and flavourings. The compositions may, if desired, be formulated in sustained release form. We prefer compositions which are designed to be taken oesophageally and to release their contents in the gastrointestinal tract.

For intravenous administration the drug may be made up as a clear sterile aqueous solution.

The dosage to be administered will of course vary with the condition to be prevented with its severity and with its location. The dosage to be administered will also vary with the mode of administration. However in general a dosage of from about 5 to 2000, preferably 10 to 1000 more preferably 100 to 1000 and most preferably 500 to 1000 mg of the drug (measured as the sodium salt of the compound of formula I) may be administered up to 2 hours before, together with, or up to 2 hours after food. The dosage may if desired be repeated several, e.g. four, times a day, a suitable total daily dosage being in the range 5 to 4000 mg. The dosage is preferably continued over a prolonged period, e.g. of greater than 48 hours.

Specific conditions which may be treated by the method of the invention include peptic, duodenal, gastric, recurrant or stormal ulceration, dyspepsia, duodenitis, Zollinger-Ellison syndrome, reflux oesophagitis and the management of haemorrhage, e.g. from erosion or ulcers, in the upper gastrointestinal tract, especially when a major blood vessel is not involved. The method of the invention may also be used to reduce the chance of haemorrhage in patients with severe hepatic failure who are known to be at special risk. The method of the invention may be used to treat the above conditions whether or not they are associated with excess gastric acid secretion. The method of the invention is mainly applicable to the treatment of men.

The compound of formula I, and pharmaceutically acceptable derivatives thereof, may also be used in admixture with or sequentially with, other compounds which are useful in the treatment of the above conditions, for example with an antacid, e.g. aluminium or magnesium hydroxide, or with an antimuscarinic agent, e.g. atropine or propantheline.

The invention is illustrated but in no way limited by the following Examples.

EXAMPLE 1

Methods (1) Anaesthetised rats

Male rats (200–300 g) were starved for 18 hours before being anaesthetised with urethane (1.7 g/kg i.p.). A jugular vein was cannulated for drug infusions and injections, and the stomach was prepared for perfusion as described by Ghosh and Schild Br J Pharmac., 13, 54–61 (1958). The stomach was perfused with 5% dextrose solution at 37° C. at a rate of 2 ml/min. The effluent perfusate was led to a pH electrode and a continuous record was made of pH and, by means of an anti-log unit, hydrogen ion concentration.

(2) Dogs

Beagle dogs of either sex, weighing 12–15 kg were anaesthetised with thiopentone sodium (25 mg/kg i.v.), a cuffed endotracheal tube inserted and anaesthesia maintained with 1% halothane in a 2:1 $N_2O/O_2$ mixture. An Andersens tube was passed into the stomach via the pharynx and the optimum position determined by means of a water recovery test in which at least 18 ml of a 20 ml bolus of water given through the tube could be recovered.

Gastric juice was then continuously aspirated using a Watson-Marlow pump and collected for 15 minute periods. The volume and pH of fluid collected in each 15 minute period were measured and a sample was titrated against 0.1 N NaOH to determine acid content using a Radiometer Autoburette. Drugs were administered via a catheter in either a cephalic or a saphenous vein. Blood pressure was measured from a catheter in a femoral artery and heart rate recorded by means of a ratemeter triggered by the blood pressure pulse. Body temperature was maintained within 38.5±1.0° C. throughout the experiments.

Materials

Pentagastrin (Peptavlon, ICI Ltd)
Histamine acid phosphate (Doses of histamine are quoted in terms of histamine base).

Results

Histamine, infused in dogs at a rate of 100 μg/kg/hr, produced a flow of gastric juice which was similar in volume and $H^+$ concentration to that due to pentagastrin at an infusion rate of 4 μg/kg/hr. Thus, in four dogs, the mean volume of gastric juice during histamine infusion was 0.64±0.06 ml/min and the mean $H^+$ concentration was 135±1.6 m Eq/l. Infusion of a solution of the sodium salt of the free acid of formula I at a rate of 5 mg/kg/hr for one hour reduced the response to histamine, the maximum effect being a 50% reduction in $H^+$ output in the samples collected in the fourth 15-min period of the infusion.

Infusion of a solution of the sodium salt of the free acid of formula I at a rate of 2.5 mg/kg/hr reduced the response to pentagastrin (4 micro g/kg/hr) by about 40% $H^+$, the peak effect appearing after 15–30 minutes of infusion.

The sodium salt of the free acid of formula I (5 mg/kg/hr) administered by continuous intravenous infusion reduced the response to pentagastrin by 40% in rats. There was no significant reduction in the response to histamine.

TABLE 1

Effects of the sodium salt of the free acid of formula I (5 mg/kg/hr) on gastric acid secretion in response to various stimuli. $H^+$ concentrations are in mM (M ± SEM).

| Secretagogue | $H^+$ during control period | Minimum $H^+$ during infusion | No. of Experiments |
|---|---|---|---|
| Histamine (3 mg/kg/hr) | 1.97 ± 0.35 | 1.79 ± 0.34 | 4 |
| Pentagastrin (3.75 μg/kg/hr) | 1.85 ± 0.41 | 1.12 ± 0.25* | 4 |

*Paired t-test, P<0.05.

EXAMPLE 2

Clinical Evaluation

Eight subjects, of either sex, who have undergone a pentagastrin test previously were selected. The subjects gave consent in writing following an explanation by the doctor in charge of the study as to the nature and purpose of the study.

Experimental Design

Subjects took the sodium salt of the free acid of formula I (active agent) orally for five days immediately prior to the day of the pentagastrin test, and then on the day of the test received the active agent by slow intravenous infusion.

The infusion of active agent began 30 minutes before the start of the pentagastrin infusion, and continued for a further 60 minutes so that for the latter period the active agent and the secretagogue were infused simultaneously.

Treatments

The table below shows the dosage regimes used in the study. Both infusions were made up using normal saline.

| Compound | Route | Dose | Duration of Administration |
|---|---|---|---|
| Pentagastrin | i.v. | 0.3 μg/kg/h | 2 hours |
| Active agent | i.v. | 3.5 mg/kg/h | 1.5 hours |
| Active agent | oral | 0.5 g q.i.d. | 5 days |

For oral administration the active agent was used in rice paper cachets each containing 0.5 g of drug, and subjects took one cachet four times a day. The first dose was taken before breakfast and the last dose of the day just before bedtime. The other doses were taken mid-morning and mid-afternoon.

Method

Subjects took the active agent as described above for five days, and then having fasted from mid-night on study day 5 were on the morning of the study day 6 intubated using a 14F Levins tube, the tube being positioned in the stomach without radiological control.

Following intubation an intravenous cannula was inserted into a vein on each forearm, one for the administration of active agent, and the other for pentagastrin. With the subject semi-recumbent gastric juices were collected in 15 minute samples by continuous manual sunction throughout the period of pentagastrin administration. The volume of each 15 minute sample was read and following filtration, acid concentration was determined by titration with 0.1 M sodium hydroxide to pH 7 using a glass pH electrode and an automatic titrator.

In eight of the subjects administration of the active agent reduced the pentagastrin stimulated acid secretion by between 30 and 75%.

I claim:

1. A method for reducing the excessive secretion of gastric acid in a patient suffering from such condition, which method comprises administering to said patient a compound of the formula I,

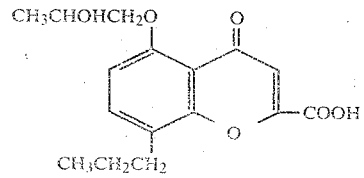

or a pharmaceutically acceptable salt, ester, or amide thereof, in an amount sufficient to reduce said secretion.

2. A method according to claim 1, wherein the active ingredient is administered rectally or orally.

3. A method according to claim 1, wherein a dosage of from 5 to 2000 mg of active ingredient, measured as the sodium salt of the compound of formula I, is administered.

4. A method according to claim 3, wherein a dosage of from 10 to 1000 mg of active ingredient is administered.

5. A method according to claim 4, wherein a dosage of from 100 to 1000 mg of active ingredient is administered.

6. A method according to claim 5, wherein a dosage of from 500 to 1000 mg of active ingredient is administered.

7. A method according to claim 1, wherein the administration is continued over a period of at least 48 hours, at a daily dosage rate of 5 to 4000 mg of active ingredient, measured as the sodium salt of the compound of formula I.

8. A method according to claim 1, wherein the active ingredient is used in admixture with, or sequentially with an antacid or an antimuscarinic agent.

* * * * *